United States Patent [19]

Tenten et al.

[11] Patent Number: 5,583,086
[45] Date of Patent: *Dec. 10, 1996

[54] CESIUM CONTAINING MULTIMETAL OXIDE CATALYST COMPOSITIONS FOR THE PREPARATION OF METHACROLEIN BY GAS-PHASE-CATALYTIC OXIDATION

[75] Inventors: Andreas Tenten, Neustadt; Hans-Peter Neumann, Mannheim; Herbert Exner, Waldsee, all of Germany

[73] Assignee: BASF Aktiengesellschaft, Ludwigshafen, Germany

[ * ] Notice: The term of this patent shall not extend beyond the expiration date of Pat. No. 5,364,825.

[21] Appl. No.: 202,067

[22] Filed: Feb. 25, 1994

[30] Foreign Application Priority Data

Mar. 9, 1993 [DE] Germany .......................... 43 07 381.6

[51] Int. Cl.$^6$ .............................. B01J 23/18; B01J 23/22; B01J 23/28
[52] U.S. Cl. .................... 502/249; 502/204; 502/205; 502/243; 502/254; 502/255; 502/311; 502/344; 568/476; 568/477; 568/479; 568/480; 568/481
[58] Field of Search .................................. 502/249, 254, 502/255, 243, 311, 313, 317, 344, 353, 205, 204

[56] References Cited

U.S. PATENT DOCUMENTS

| | | | |
|---|---|---|---|
| 4,148,757 | 4/1979 | Brazdil et al. | 502/205 |
| 4,212,766 | 7/1980 | Brazdil et al. | 502/204 |
| 4,925,823 | 5/1990 | Krabetz et al. | 502/311 |
| 5,173,468 | 12/1992 | Boehning et al. | 502/317 |
| 5,364,825 | 11/1994 | Neumann et al. | 502/311 |

FOREIGN PATENT DOCUMENTS

| | | |
|---|---|---|
| 000835 | 2/1979 | European Pat. Off. . |
| 3338380 | 4/1984 | Germany . |

*Primary Examiner*—Asok Pal
*Attorney, Agent, or Firm*—Oblon, Spivak, McClelland, Maier & Neustadt, P.C.

[57] ABSTRACT

Cesium based multimetal oxide compositions which are suitable as catalysts for the gas-phase-catalytic oxidative preparation of methacrolein from isobutene or tert-butanol or its methyl ether. The catalysts are characterized by increased selectivity for the formation of methacrolein. The catalysts have locally delimited regions of an oxide composition, preferably ($Bi_2W_2O_9$), surrounded by the remaining constituents of the multimetal oxide.

20 Claims, No Drawings

CESIUM CONTAINING MULTIMETAL OXIDE CATALYST COMPOSITIONS FOR THE PREPARATION OF METHACROLEIN BY GAS-PHASE-CATALYTIC OXIDATION

SUMMARY OF THE INVENTION

The present invention relates to multimetal oxide compositions of the formula I $$[X_a^1 X_b^2 O_x]_p [X_c^3 X_d^4 X_e^5 X_f^6 X_g^7 X_h^2 O_y]_q \quad (I),$$

where
- $X^1$ is bismuth, tellurium, antimony, tin and/or copper,
- $X^2$ is molybdenum and/or tungsten,
- $X^3$ is cesium,
- $X^4$ is an alkaline earth metal, nickel, cobalt, copper, manganese, zinc, tin, cadmium and/or mercury,
- $X^5$ is iron, chromium, cerium and/or vanadium,
- $X^6$ is phosphorus, arsenic, boron and/or antimony,
- $X^7$ is a rare-earth metal, titanium, zirconlure, niobium, tantalum, rhenium, ruthenium, rhodium, silver, gold, aluminum, gallium, indium, silicon, germanium, lead, thorium and/or uranium,
- a is from 0.01 to 8,
- b is from 0.1 to 30,
- c is from h/20 to h/6, preferably from h/15 to h/10,
- d is from 0 to 20,
- e is from 0 to 20,
- f is from 0 to 6,
- g is from 0 to 15,
- h is from 8 to 16,
- x and y are numbers determined by the valency and frequency of the elements in I other than oxygen and
- p and q are numbers other than zero whose ratio p/q is from 0.1 to 10, preferably from 0.1 to 5, which contain the moiety $$[X_a^1 X_b^2 O_x]_p$$

in the form of three-dimensional regions, delimited from their local environment due to their chemical composition, which differs from their local environment, of the chemical composition $$X_a^1 X_b^2 O_x$$

whose maximum diameter (longest line passing through the center of gravity of the region and connecting two points on the surface (interface) of the region) is from >0 to 200 μm, advantageously from 0.1 to 100 μm, preferably from 1 to 25 μm, particularly preferably from 5 to 15 μm.

The present invention also relates to a process for the preparation of these compositions, and to their use (the experimental determination of the maximum diameter is carried out, for example, by energy-dispersive X-ray analysis (EDXS), for example using a JEOL JCXA/733 electron beam microprobe).

BACKGROUND OF THE INVENTION

EP-A 835 relates to compositions of the formula I and states that $X^3$ is particularly advantageously K, Rb and/or Cs. In all of the working examples, $X^3$ is exclusively K. With respect to the preparation of these compositions, EP-A 835 recommends first preparing the mixed oxide $$X_a^1 X_b^2 O_x$$

in the absence of the other constituents of the compositions I, mixing this oxide, after its preparation with sources of the other constituents of the compositions I, and drying and calcining the mixture.

Furthermore, EP-A 835 relates to the use of such compositions as catalysts for the gas-phase-catalytic oxidation or ammonoxidation of olefins. However, the multimetal oxide compositions disclosed in EP-A 835 have the disadvantage that, when they are used as catalysts for the gas-phase-catalytic oxidation of isobutene or tert-butanol to methacrolein, the selectivity of methacrolein formation is not entirely satisfactory.

DE-C 3 338 380 discloses compositions of the formula I where $X^3$=Cs, but in all cases c<h/20. They are obtained by first mixing a bismuth compound and a tungsten compound in an aqueous medium, drying the aqueous mixture, calcining the resultant composition at from 600° to 900° C. and subsequently powdering the calcined composition so that the particle size is less than 150 μm, mixing the resultant powder with an aqueous solution of the sources of the other constituents of the multimetal oxide composition, evaporating the resultant mixture, shaping and calcining the residue. Furthermore, DE-C 3 338 380 recommends the use of these compositions as catalysts for the gas-phase-catalytic oxidative preparation of (meth) acrolein and (meth) acrylic acid. However, these multimetal oxide compositions disclosed in DE-C 3 338 380 have the disadvantage that, when they are used for the gas-phase-catalytic oxidative preparation of methacrolein from isobutene or tert-butanol, the selectivity of methacrolein formation is not entirely satisfactory.

The earlier application DE-A 42 20 859 (O.Z. 0050/43345) relates to compositions of the formula I, containing three-dimensional regions of the chemical composition $$X_a^1 X_b^2 O_x$$

whose maximum diameter is from 1 to 25 μm. This earlier application recommends that $X^3$ is an alkali metal, thallium and/or samarium. In all the working examples, the alkali metal is potassium. In addition, this earlier application recommends the use of these multimetal oxide compositions as, inter alia, catalysts for the gas-phase-catalytic oxidative preparation of (meth)acrolein. However, the K-containing multimetal oxide compositions of the earlier application DE-A 42 20 859 (O.Z. 0050/43345) have the disadvantage that, when they are used for the gas-phase-catalytic oxidative preparation of methacrolein from isobutene or tert-butanol, the selectivity of the methacrolein formation is not entirely satisfactory.

OBJECT OF THE INVENTION

It is an object of the present invention to provide multimetal oxide compositions which do not have the disadvantage of the multimetal oxide compositions of the prior art.

We have found that this object is achieved by the compositions defined at the outset.

DESCRIPTION OF THE PREFERRED EMBODIMENTS

Preferred compositions I are those which contain at least one of the elements iron, chromium, cerium, vanadium or another rare-earth metal with a stoichiometric coefficient which is not 0, advantageously ≧0.01.

Particularly advantageous compositions I according to the invention are those in which $X^1$ is bismuth. Of these, preference is in turn given to those which conform to the formula II $$[Bi_{a'}Z_{b'}^2O_{x'}]_{p'}[Z_{12}^2,Z_{c'}^3,Z_{d'}^4,Fe_{e'},Z_{f'}^5,Z_{g'}^6,Z_{h'}^7,O_{y'}]_{q'} \quad (II),$$

where $Z^2$ is molybdenum and/or tungsten $Z^3$ is cesium $Z^4$ is nickel and/or cobalt, $Z^5$ is phosphorus, arsenic, boron, antimony, tin, cerium and/or lead, $Z^6$ is silicon, aluminum, titanium and/or zirconium, $Z^7$ is copper, silver and/or gold, a' is from 0.1 to 1, b' is from 0.2 to 2, c' is from 0.6 to 2, preferably from 0.8 to 1.2, d' is from 3 to 10, e' is from 0.01 to 5, preferably from 0.1 to 3, f' is from 0 to 5, g' is from 0 to 10, h' is from 0 to 1 and x' and y' are numbers determined by the valency and frequency of the elements in II other than oxygen, and p' and q' are numbers other than zero whose ratio p'/q' is 0.1 to 5, preferably from 0.5 to 2, very particularly preferred compositions II being those in which $Z_{b'}^2=(tungsten)_{b'}$ and $Z_{12}^2=(molybdenum)_{12}$.

The compositions I (compositions II) according to the invention furthermore prove to be more advantageous the higher the percentage of the number of various maximum diameters which has a value in the range from 1 to 25 μm (preferably from 1 to 20 μm, particularly preferably from 5 to 15 μm).

This means that it is preferred for at least half the maximum diameters to be in the range from 1 to 25 μm (advantageously in the range from 1 to 20 μm, very particularly preferably in the range from 5 to 15 μm), and it is very particularly preferred for all the maximum diameters to be in this range.

In addition, the phases $$X_a^1X_b^2O_x$$

are preferably those having the stoichiometry $BiZ^2O_6$, $Bi_2Z_2^2O_9$ and/or $Bi_2Z_3^2O_{12}$, of which $$Bi_2Z_2^2O_9$$

is preferred, in particular when $Z^2$=tungsten.

The compositions I according to the invention are obtainable in a simple manner, for example, by first preparing a finely divided oxometallate $$X_a^1X_b^2O_x$$

in a manner known per se (cf. EP-A 835, DE-C 3 338 380 and the earlier application DE-A 42 20 859 (O.Z. 0050/ 43345), converting this oxometallate into an intimate dry mix with suitable sources (cf. EP-A 835, DE-C 3 338 380 and the earlier application DE-A 42 20 859 (O.Z. 0050/ 43345)) of the remaining constituents of the desired composition according to the invention in the necessary amounts, and subsequently calcining this dry mix for several hours (normally in a stream of air), expediently at from 400° to 600° C. In a less preferred embodiment, the oxometallate $$X_a^1X_b^2O_{x'}$$

preferably pre-calcined, is intimately mixed with sources of the remaining constituents of the desired compositions according to the invention in a liquid, preferably aqueous, medium. This mixture is subsequently dried to give an intimate dry mix, which is then calcined as described above.

However, the compositions I according to the invention are particularly advantageously obtainable by first forming an oxometallate $$X_a^1X_b^2O_{x'}$$

preferably calcined, in a manner known per se (for example by mixing water-soluble salts of $X^1$, such as nitrates, carbonates, hydroxides or acetates, with $X^2$-acids or ammonium salts thereof in water, drying (preferably spray-drying) the mixture, and calcining the dried composition), comminuting the composition (for example in a ball mill or by jet grinding), separating the particle class having a maximum particle diameter in the maximum diameter range desired for the composition I from the resultant powder, generally comprising substantially spherical particles, by a known classification method (for example wet or dry screening), and preferably mixing this particle class with, preferably, from 0.1 to 3% by weight, based on the weight of this separated particle class, of finely divided $SiO_2$ (the number average maximum particle diameter of the $SiO_2$ particles, which are usually essentially spherical, is expediently from 10 to 50 nm), giving a starting composition 1.

The calcination temperature is expediently from 400° to 900° C., preferably from 600° to 900° C., in particular when $X^1$=Bi and $X^2$=W. The calcination is usually carried out in a stream of air. The calcination duration is generally a few hours.

A very intimate, preferably finely divided dry mix of the other constituents of the desired composition according to the invention is prepared starting from sources which are suitable in a manner known per se (for example by combining water-soluble salts, such as halides, nitrates, acetates, carbonates or hydroxides, in an aqueous solution and subsequently spray-drying the aqueous solution, or suspending water-insoluble salts, for example oxides, in an aqueous medium and subsequently spray-drying the suspension), this dry mix being referred to here as starting composition 2.

The only essential feature is, as is generally known, that the constituents of the starting composition 2 are either already oxides or are compounds which can be converted into oxides by heating, if necessary in the presence of oxygen. The starting composition 1 and the starting composition 2 are subsequently mixed with one another in the desired mixing ratio, compacted, preferably by pressing, and then calcined, as described above, expediently at from 400° to 600° C. (normally in a stream of air) for several hours.

In the case of unsupported catalysts, the pressing gives the desired catalyst geometry directly, preference being given to hollow cylinders having an external diameter and a length of from 2 to 10 mm and a wall thickness of from 1 to 3 mm.

Very generally, the compositions I according to the invention can be shaped either before or after the calcination. This can also be effected, for example, by comminuting the active compositions I according to the invention after calcination and applying them to inert supports to give supported catalysts. The application can also be carried out before the final calcination. In this case, the application is preferably carried out as described in EP-B 293 859. Preferred supports are spherical inert materials (for example porous or non-porous aluminum oxides, silicon dioxide, thorium dioxide, zirconium dioxide, silicon carbide or silicates, such as magnesium silicate or aluminum silicate) having a diameter of from 1 to 5 mm. In general, the support beads coated with active composition contain from 20 to 50% by weight of active composition. Significantly, the selectivity in the formation of methacrolein when the compositions according to the invention are used in the form of such supporting catalysts has particularly high values. The compositions I according to the invention preferably have a specific surface area, a specific total pore volume and a pore diameter distribution as described in EP-B 293 859. It is of course also possible for the compositions I according to the invention to be employed in powder form.

The compositions I according to the invention are particularly suitable as catalysts of increased selectivity for the gas-phase-catalytic oxidation of isobutene or tert-butanol to methacrolein. This also applies when the tert-butanol is used in masked form, for example in the form of its methyl ether. However, they are also suitable for the gas-phase-catalytic oxidation of other organic compounds, such as, in particular, other alkanes, alkanols, alkanals, alkenes and alkenals, preferably having 3 to 6 carbon atoms, to olefinically unsaturated aldehydes and/or carboxylic acids and to the corresponding nitriles (ammonoxidation, in particular of propene to acrylonitrile and of isobutene or tert-butanol to methacrylonitrile). They are also suitable for the oxidative dehydrogenation of organic compounds.

The oxidant used, in a manner known per se, for the gas-phase-catalytic oxidative preparation of methacrolein from isobutene or tert-butanol (including its methyl ether form) is oxygen, expediently diluted with inert gases. Examples of suitable inert gases are $N_2$, $CO_2$, hydrocarbons and/or steam. The reaction temperature and pressure are known to persons skilled in the art.

EXAMPLES a) Preparation of a Starting Composition 1

6.7 kg of finely divided $H_2WO_4$ were added to 50 kg of a solution of $Bi(NO_3)_3$ in aqueous nitric acid (11% by weight of Bi, 6.4% by weight of $HNO_3$, in each case based on the solution), and the mixture was stirred at 50° C. for 1 hour.

The resultant suspension was spray-dried (inlet temperature 300° C., outlet temperature 100° C.) and calcined at 750° C. for 2 hours in an air-charged rotary kiln. The resultant preformed calcined mixed oxide ($Bi_2W_2O_9$ with a small amount of $WO_3$ impurity) was ground, and a particle fraction PF whose maximum diameter was in the range of 5 to 15 µm was removed from the ground material by classification (wet screening). The particle fraction PF was subsequently combined with 1% of its weight of finely divided, essentially spherical $SiO_2$ (number average maximum diameter 28 nm).

b) Preparation of a Starting Composition 2

A solution of 1309 g of ammonium heptamolybdate tetrahydrate in 4 l of water was mixed with 30.4 g of a 47.3% strength by weight (based on the KOH solution) K-containing aqueous potassium hydroxide solution, and the mixture was warmed to 40° C. 1587 g of a 12.6% strength by weight Co-containing aqueous $Co(NO_3)_2$ solution and 764.4 g of a 13.5% strength by weight Fe-containing aqueous $Fe(NO_3)_3$ solution, both of which had been prewarmed to 40° C., were subsequently added to this mixture over the course of 20 minutes. The mixture was subsequently stirred for a further 5 minutes, and 113.8 g of an aqueous mixture containing 52% of its weight of colloidal $SiO_2$ was subsequently added (over the course of 5 minutes). After the aqueous mixture had been stirred for a further 5 minutes, it was spray-dried at an inlet temperature of 380° C. and an outlet temperature of 130° C.

c) Preparation of Novel Compositions I (NC1 to NC5) and Comparative Compositions (CC1 to CC4)

CC1: The starting compositions 1 and 2 were mixed in the ratio necessary to give the composition

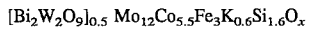
$[Bi_2W_2O_9]_{0.5} Mo_{12}Co_{5.5}Fe_3K_{0.6}Si_{1.6}O_x$ the mixture was pressed to give hollow cylinders having a length of 7 mm, an external diameter of 7 mm and a wall thickness of 2 mm, and the cylinders were subsequently calcined in an air-charged fan-assisted oven at 450° C. for 6 hours. Energy-dispersive X-ray analysis (EDXS) of this and the subsequent multimetal oxide composition using a JEOL JCXA/733 electron beam microprobe showed that these multimetal oxide compositions contain three-dimensional regions of the chemical composition $Bi_2W_2O_9$ which are delimited from their local environment due to their chemical composition, which is different from their local environment, and whose maximum diameters essentially corresponded to the maximum particle diameters of the particle fraction PF used for their preparation.

NC1: As CC1, but the starting composition 2 was one prepared using 113.4 g of a 43.3% strength by weight Cs-containing aqueous cesium hydroxide solution instead of the aqueous potassium hydroxide solution. The resultant composition according to the invention was as follows:

$[Bi_2W_2O_9]_{0.5} Mo_{12}Co_{5.5}Fe_3Cs_{0.6}Si_{1.6}O_x$

NC2: As CC1, but the starting composition 2 was one prepared using 189 g of a 43.3% strength by weight Cs-containing aqueous cesium hydroxide solution instead of the aqueous potassium hydroxide solution. The resultant composition according to the invention was as follows:

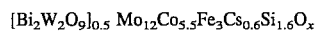
$[Bi_2W_2O_9]_{0.5} Mo_{12}Co_{5.5}Fe_3Cs_{1.0}Si_{1.6}O_x$

NC2T: As NC2, but the mixture of starting compositions 1 and 2 was not pressed to give hollow cylinders, but instead immediately calcined in an air-charged fan-assisted oven at 450° C. for 6 hours, and the resultant active composition, after comminution, was applied in a manner known per se to inert support beads (steatite beads having a diameter of from 2 to 3 mm). The resultant supported catalyst contained 36.5% by weight of active composition.

NC3: As CC1, but the starting composition 2 was one prepared using 283.5 g of a 43.3% strength by weight Cs-containing aqueous cesium hydroxide solution instead of the aqueous potassium hydroxide solution. The resultant composition according to the invention was as follows:

$[Bi_2W_2O_9]_{0.5} Mo_{12}Co_{5.5}Fe_3Cs_{1.5}Si_{1.6}O_x$

CC2: As CC1, but the starting composition 2 was one prepared using 50.6 g of the 47.3% strength by weight K-containing aqueous potassium hydroxide solution and only 382.2 g of the 13.5% strength by weight Fe-containing aqueous $Fe(NO_3)_3$ solution. The resultant composition was as follows:

$$[Bi_2W_2O_9]_{0.5} Mo_{12}Co_{5.5}Fe_{1.5}K_{1.0}Si_{1.6}O_x$$

NC4: As CC2, but the aqueous potassium hydroxide solution used in the preparation of the starting composition 2 was replaced by 189 g of the 43.3% strength by weight Cs-containing aqueous cesium hydroxide solution.

The resultant composition according to the invention was as follows:

$$[Bi_2W_2O_9]_{0.5} Mo_{12}Co_{5.5}Fe_{1.5}Cs_{1.0}Si_{1.6}O_x$$

NC5: Example 15 of DE-C 3 338 380 was repeated, but the 48.7 g of cesium nitrate were replaced by 58.4 g of cesium nitrate.

The resultant composition was as follows:

$$Bi_2W_{2.4}Fe_{1.6}Mo_{12}Co_6Si_{1.0}Cs_{0.6}O_x$$

CC3: Example 15 of DE-C 3 338 380 was repeated exactly as described therein.

The resultant composition was as follows:

$$Bi_2W_{2.4}Fe_{1.6}Mo_{12}Co_6Si_{1.0}Cs_{0.5}O_x$$

CC4: Example 15 of DE-C 3 338 380 was repeated, but the 48.7 g of cesium nitrate were replaced by 43.9 g of $RbNO_3$.

The resultant composition was as follows:

$$Bi_2W_{2.4}Fe_{1.6}Mo_{12}Co_6Si_{1.0}Rb_{0.6}O_x$$

d) Gas-Phase-Catalytic Oxidation of isobutene/tert-butanol/methyl ether of tert-butanol A reaction tube (V2A, wall thickness 2 mm, internal diameter 25 mm, salt-bath temperature control) filled in each case with 1000 g of the respective multimetal oxide composition from c) was charged with a gas mixture having the composition 4% by volume of isobutene (tert-butanol or its methyl ether (MTBE)), 7.5% by volume of oxygen, 5% by volume of steam and 83.5% by volume of nitrogen. The charge B was in most cases adjusted to a value of about 0.22 (amount of starting compound in grams per hour and per gram of catalyst).

The salt-bath temperature was in all cases adjusted so that a conversion U of the $C_4$ starting compound of about 97.5 mol % resulted for a single pass. It was in all cases about 340° C.

The selectivities for the formation of methacrolein ($S_{MAC}$) and methacrylic acid ($S_{MAA}$) resulting in this respect as a function of the multimetal oxide composition employed in each case are shown in the table below.

| Multimetal oxide composition | B | Starting compound | U (mol %) | $S_{MAC}$ (mol %) | $S_{MAA}$ (mol %) |
|---|---|---|---|---|---|
| CC1 | 0.22 | tert-butanol | 98 | 72.7 | 3.4 |
| NC1 | 0.20 | tert-butanol | 97.6 | 76.8 | 3.8 |
| NC2 | 0.38 | isobutene | 97.3 | 83.2 | 1.9 |
| NC2 | 0.23 | tert-butanol | 97.5 | 80.1 | 2.0 |
| NC3 | 0.25 | tert-butanol | 97.4 | 78.8 | 1.6 |
| CC2 | 0.22 | tert-butanol | 97.6 | 70.1 | 2.9 |
| NC4 | 0.20 | tert-butanol | 98.0 | 71.2 | 2.6 |

-continued

| Multimetal oxide composition | B | Starting compound | U (mol %) | $S_{MAC}$ (mol %) | $S_{MAA}$ (mol %) |
|---|---|---|---|---|---|
| NC5 | 0.20 | tert-butanol | 96.2 | 76.2 | 2.5 |
| CC3 | 0.22 | tert-butanol | 97.0 | 73.6 | 2.4 |
| CC4 | 0.21 | tert-butanol | 96.8 | 72.7 | 2.5 |
| NC2 | 0.39 | MTBE | 97.8 | 82.6 | 3.6 |
| NC2T | 0.2 | MTBE | 97.7 | 84.2 | 2.5 |

As can be seen, increased values for $S_{MAC}$ result on use of the multimetal oxide compositions according to the invention. After an operating time of 500 hours, the composition NC1 employed was again subjected to energy-dispersive X-ray analysis, which showed that the chemically delimited regions of composition $Bi_2W_2O_9$ were essentially unchanged with respect to their maximum diameters.

We claim:

1. A multimetal oxide composition of the formula I $$(X_a^1 X_b^2 O_x)_p (X_c^3 X_d^4 X_e^5 X_f^6 X_g^7 X_h^2 O_y)_q \qquad (I)$$

where $X^1$ is bismuth, tellurium, antimony, tin and/or copper, $X^2$ is molybdenum and/or tungsten, $X^3$ is cesium, $X^4$ is an alkaline earth metal, nickel, cobalt, copper, manganese, zinc, tin, cadmium and/or mercury, $X^5$ is iron, chromium, cerium and/or vanadium, $X^6$ is phosphorous, arsenic, boron and/or antimony, $X^7$ is a rare-earth metal, titanium, zirconium, niobium, tantalum, rhenium, ruthenium, rhodium, silver, gold, aluminum, gallium, indium, silicon, germanium, lead, thorium and/or uranium, a is from 0.01 to 8, b is from 0.1 to 30, c is from h/20 to h/6, d is from 0 to 20, e is from 0 to 20, f is from 0 to 6, g is from 0 to 15, h is from 8 to 16, x and y are numbers determined by the valency, presence and amount of the elements in I other than oxygen and p and q are numbers other than zero whose ratio p/q is from 0.1 to 10, which contains the moiety $$(X_a^1 X_b^2 O_x)_p$$

in the form of locally differentiated, three-dimensional regions, which differ from their local environment as a result of their chemical composition, $$X_a^1 X_b^2 O_x,$$

which chemical composition is different from that of their local environment, the maximum diameter of said three-dimensional regions, as measured by the longest line passing through the center of gravity of a region and connecting two points on the surface or interface of the region, being from >0 to 200 μm.

2. A multimetal oxide composition as claimed in claim 1, whose stoichiometric coefficient c is from h/15 to h/10.

3. A multimetal oxide composition as claimed in claim 1, in which all the locally delimited regions of the composition $X_a^1X_b^2O_x$ have a maximum diameter in the range from 1 to 25 μm.

4. A multimetal oxide composition as claimed in claim 1, in which $X^1$ is bismuth.

5. A multimetal oxide composition as claimed in claim 1, in which $X_a^1X_b^2O_x$ is identical with the $Bi_2W_2O_9$.

6. The multimetal oxide composition of claim 1, wherein the $X_a^1X_b^2O_x$ moiety is a composition selected from the group consisting of $BiZ^2O_6$, $BiZ_2^2O_9$ and $Bi_2Z_3^2O_{12}$, wherein $Z^2$ is tungsten.

7. A process for the gas-phase-catalytic oxidative preparation of methacrolein from tert-butanol, its methyl ether and/or isobutene, wherein the catalyst used is a multimetal oxide composition as claimed in claim 1.

8. A multimetal oxide composition of the formula I as defined in claim 1 synthesized by preparing a first finely divided oxometallate $X_a^1X_b^2O_x$ forming a dry powder of said oxometallate and converting said dry powder into an intimate dry mix with sources of the remaining constituents, $X_c^3X_d^4X_e^5X_f^6X_g^7X_h^2O_y$, of the multimetal oxide composition, and subsequently calcining this intimate dry mixture.

9. A multimetal oxide composition as set forth in claim 1 in which at least half of the locally delimited regions of the composition $X_a^1X_b^2O_x$ have a maximum diameter in the range from 1 to 25 μm.

10. A multimetal oxide composition as set forth in claim 1 in which at least half of the locally differentiated three-dimensional regions of said composition $X_a^1X_b^2O_x$ have a maximum diameter in the range from 5 to 15 μm.

11. The catalyst composition of claim 1, wherein $X^1$ is Bi and $X^2$ is tungsten.

12. The multimetal oxide composition of the formula I $(X_a^1X_b^2O_x)_p (X_c^3X_d^4X_e^5X_f^6X_g^7X_h^2O_y)_q$ (I)

wherein
 $X^1$ is bismuth,
 $X^2$ is molybdenum and/or tungsten,
 $X^3$ is cesium,
 $X^4$ is cobalt,
 $X^5$ is iron,
 $X^6$ is phosphorous,
 $X^7$ is silicon,
 a is from 0.01 to 8,
 b is from 0.1 to 30,
 c is from h/20 to h/6,
 d is from 0 to 20,
 e is from 0 to 20,
 f is 0,
 g is from 0 to 15,
 h is from 8 to 16,
 x and y are numbers determined by the valency, presence and amount of the elements in I other than oxygen and p and q are numbers other than zero whose ratio p/q is from 0.1 to 10, which contains the moiety $(X_a^1X_b^2O_x)_p$ in the form of locally differentiated, three-dimensional regions, which differ from their local environment as a result of their chemical composition, $X_a^1X_b^2O_x$, which chemical composition is different from that of their local environment, the maximum diameter of said three-dimensional regions, as measured by the longest line passing through the center of gravity of a region and connecting two points on the surface or interface of the region, being from >0 to 200 μm.

13. The multimetal oxide composition of claim 12 wherein
 $(X_a^1X_b^2O_x)_p$ is $(Bi_aW_bO_x)_p$
and wherein
 $(X_c^3X_d^4X_e^5X_f^6X_g^7X_h^2O_y)_q$ is
 $(X_c^3X_d^4X_e^5X_f^6X_g^7Mo_hO_y)_q$.

14. A process for the preparation of a composition of the formula I $(X_a^1X_b^2O_x)_p (X_c^3X_d^4X_e^5X_f^6X_g^7X_h^2O_y)_q$ (I)

where
 $X^1$ is bismuth, tellurium, antimony, tin and/or copper,
 $X^2$ is molybdenum and/or tungsten,
 $X^3$ is cesium,
 $X^4$ is an alkaline earth metal, nickel, cobalt, copper, manganese, zinc, tin, cadmium and/or mercury,
 $X^5$ is iron, chromium, cerium and/or vanadium,
 $X^6$ is phosphorous, arsenic, boron and/or antimony,
 $X^7$ is a rare-earth metal, titanium, zirconium, niobium, tantalum, rhenium, ruthenium, rhodium, silver, gold, aluminum, gallium, indium, silicon, germanium, lead, thorium and/or uranium,
 a is from 0.01 to 8,
 b is from 0.1 to 30,
 c is from h/20 to h/6,
 d is from 0 to 20,
 e is from 0 to 20,
 f is from 0 to 6,
 g is from 0 to 15,
 h is from 8 to 16,
 x and y are numbers determined by the valency, presence and amount of the elements in I other than oxygen, and p and q are numbers other than zero whose ratio p/q is from 0.1 to 10,
which contains the moiety $(X_a^1X_b^2O_x)_p$ in the form of three-dimensional regions, which differ from their local environment as a result of their chemical composition, $X_a^1X_b^2O_x$, comprising:
 preparing a first finely divided powder from a calcined mixed oxide having the formula $X_a^1X_b^2O_x$, said mixed oxide having a maximum particle diameter in the range from >0 to 200 μm, converting this finely divided powder into an intimate dry mix with sources of the materials used to form the remaining consitituents $(X_c^3X_d^4X_e^5X_f^6X_g^7X_h^2O_y)$ of the multimetal oxide composition in the necessary amounts, and subsequently calcining the dry mixture, preparing a second finely divided powder containing $X^3, X^4, X^5, X^6, X^7$ and $X^2$, wherein said second powder is in a form which is already oxidic and/or can be converted into oxidic form by calcination, mixing said first and said second powder to form a mixture and, calcining said mixture.

15. The process of claim 14, wherein said particles of oxometallate, $X_a^1X_b^2O_x$, are mixed with from 0.1 to 3% by weight, based on the weight of said oxometallate, of finely divided $SiO_2$ to provide a first starting composition; a second finely divided dry powder composed of the other constituents, $X_c^3X_d^4X_e^5X_f^6X_g^7X_h^2O_y$, is prepared, and said first dry powder and said second dry powder are mixed with one another and calcined at from 400° to 600° C.

16. The process of claim 14, wherein the particle diameter of the finely divided powder from a calcined mixed oxide having the formula $X_a^1X_b^2O_x$ ranges from 1 to 20 μm.

17. The process of claim 14 wherein the oxometallate $X_a^1X_b^2O_x$ is pre-calcined at a temperature of from 600° to 900° C.

18. A multimetal oxide composition of the formula II $(Bi_{a'}Z_{b'}^2,O_{x'})_{p'}(Z_{12}^2,Z_{c'}^3,Z_{d'}^4,Fe_{e'},Z_{f'}^5,Z_{g'}^6,Z_{h'}^7,O_{y'})_{q'}$  (II), where $Z^2$ is molybdenum and/or tungsten $Z^3$ is cesium $Z^4$ is nickel and/or cobalt, $Z^5$ is phosphorus, arsenic, boron, antimony, tin, cerium and/or lead, $Z^6$ is silicon, aluminum, titanium and/or zirconium, $Z^7$ is copper, silver and/or gold, a' is from 0.1 to 1, b' is from 0.2 to 2, c' is from 0.6 to 2, d' is from 3 to 10, e' is from 0.01 to 5, f' is from 0 to 5, g' is from 0 to 10, h' is from 0 to 1, x' and y' are numbers determined by the valency and frequency of the elements in II other than oxygen, and p' and q' are numbers other than zero whose ratio p'/q' is from 0.1 to 5, which contains the moiety $(Bi_{a'}Z_{b'}^2,O_{x'})_{p'}$ in the form of locally differentiated, three-dimensional regions, which differ from their local environment as a result of their chemical composition, $Bi_{a'}Z_{b'}^2,O_{x'}$ which chemical composition is different from that of their local environment, the maximum diameter of said three-dimensional regions, as measured by the longest line passing through the center of gravity of a region and connecting two points on the surface or interface of the region, being from >0 to 200 μm.

19. The multimetal oxide composition of claim 18, wherein $Bi_{a'}Z_{b'}^2,O_{x'}$ is $Bi_2Z_2^2O_9$, and $Z^2$ is molybdemum or tungsten.

20. The multimetal oxide composition of claim 1 wherein $(X_a^1X_b^2O_x)_p$ is $(Bi_aW_bO_x)_p$ and wherein
$(X_c^3X_d^4X_e^5X_f^6X_g^7X_h^2O_y)_q$ is
$(X_c^3X_d^4X_e^5X_f^6X_g^7Mo_hO_y)_q$.

* * * * *